United States Patent [19]

Comment et al.

[11] Patent Number: 4,846,184

[45] Date of Patent: Jul. 11, 1989

[54] SKIN REFLECTANCE MEASURING APPARATUS

[75] Inventors: Alain Comment, Echirolle; Yannick C. James, Cergy; Jeanine Arnaud-Battandier, Le Chesnay, all of France; Emilio Crisafulli, Milan, Italy

[73] Assignee: Sanofi, France

[21] Appl. No.: 161,407

[22] Filed: Feb. 23, 1988

Related U.S. Application Data

[63] Continuation of Ser. No. 849,446, Apr. 8, 1986, abandoned.

[30] Foreign Application Priority Data

Apr. 9, 1985 [FR] France ............................ 85 05331

[51] Int. Cl.⁴ .............................................. A61B 6/00
[52] U.S. Cl. ...................................... 128/633; 128/665; 356/445; 356/448
[58] Field of Search ............... 128/632, 633, 664, 665; 356/445, 446, 448

[56] References Cited

U.S. PATENT DOCUMENTS

| | | | |
|---|---|---|---|
| 2,315,282 | 3/1943 | Snow | 356/446 |
| 3,549,264 | 12/1970 | Christie | 356/446 |
| 3,999,864 | 12/1976 | Mutter | 356/448 |
| 4,218,144 | 8/1980 | Whitehouse | 356/446 |
| 4,344,709 | 8/1982 | Provder et al. | 356/448 |
| 4,552,458 | 11/1985 | Lowne | 356/446 |
| 4,613,235 | 9/1986 | Juga | 356/446 |

FOREIGN PATENT DOCUMENTS 2009922 6/1979 United Kingdom .

OTHER PUBLICATIONS

Physics in Medicine & Biology, vol. 25, No. 4, Jul. 1980, pp. 695–709, The Institute of Physics, Bristol, GB; J. B. Dawson et al., "A Theoretical and Experimental Study of Light Absorption and Scattering by in Vivo Skin", *pp. 700–702*.

Primary Examiner—Max Hindenburg
Assistant Examiner—John C. Hanley
Attorney, Agent, or Firm—Bacon & Thomas

[57] ABSTRACT

A probe comprising a casing of which one face which will be in contact with the skin is providied with an aperture, is connected to a measuring device by means of a flexible connection in fiber optics comprising at least three optical conductors which, at a first end, are secured in the casing of the probe such as to face the aperture thereof, the first and second conductors having their first end portions directed respectively in a first and a second directions which are symmetrical to each other with respect to an axis extending normally through the aperture, while the third conductor has its first end portion directed in another direction than said second direction.

6 Claims, 5 Drawing Sheets

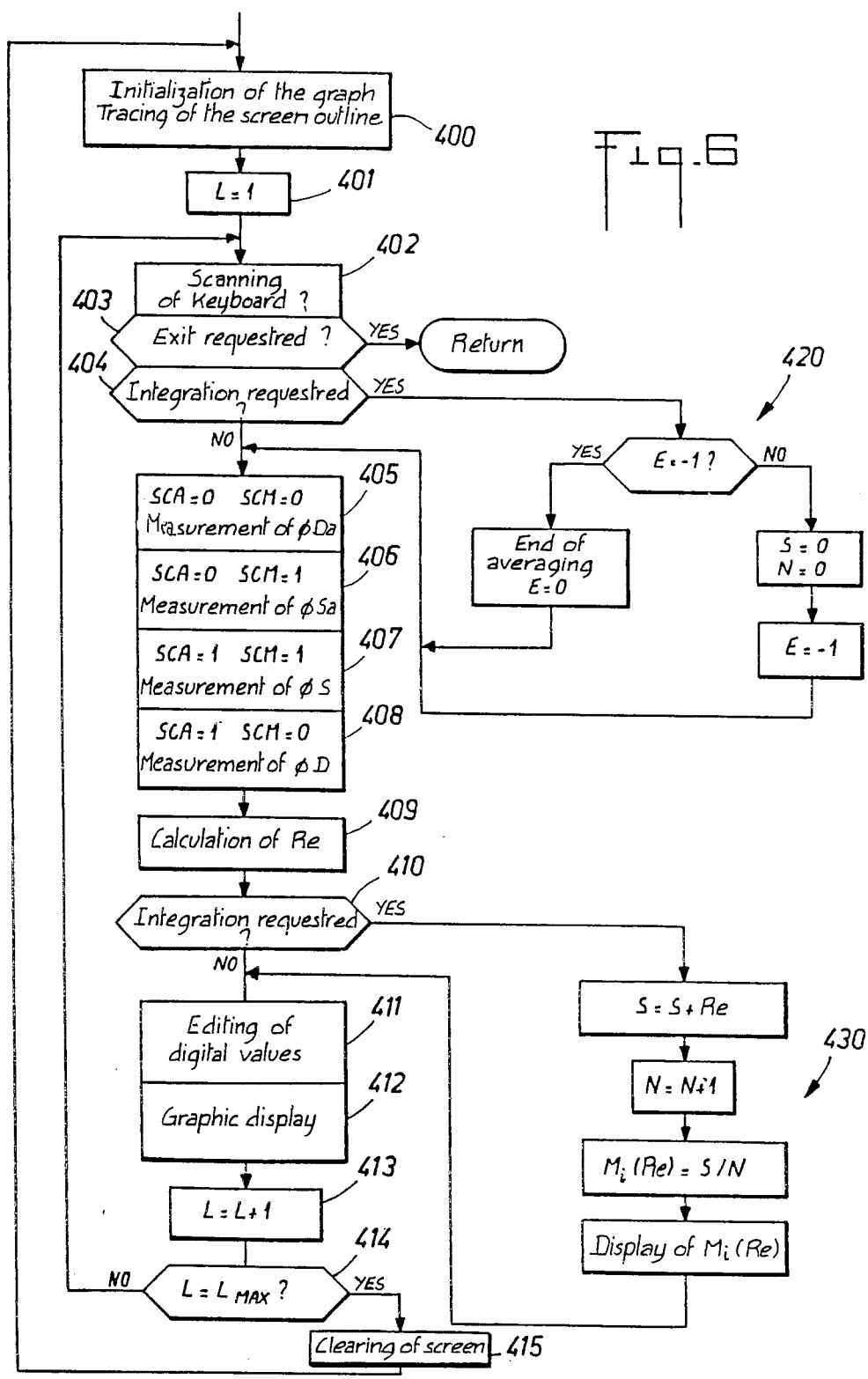

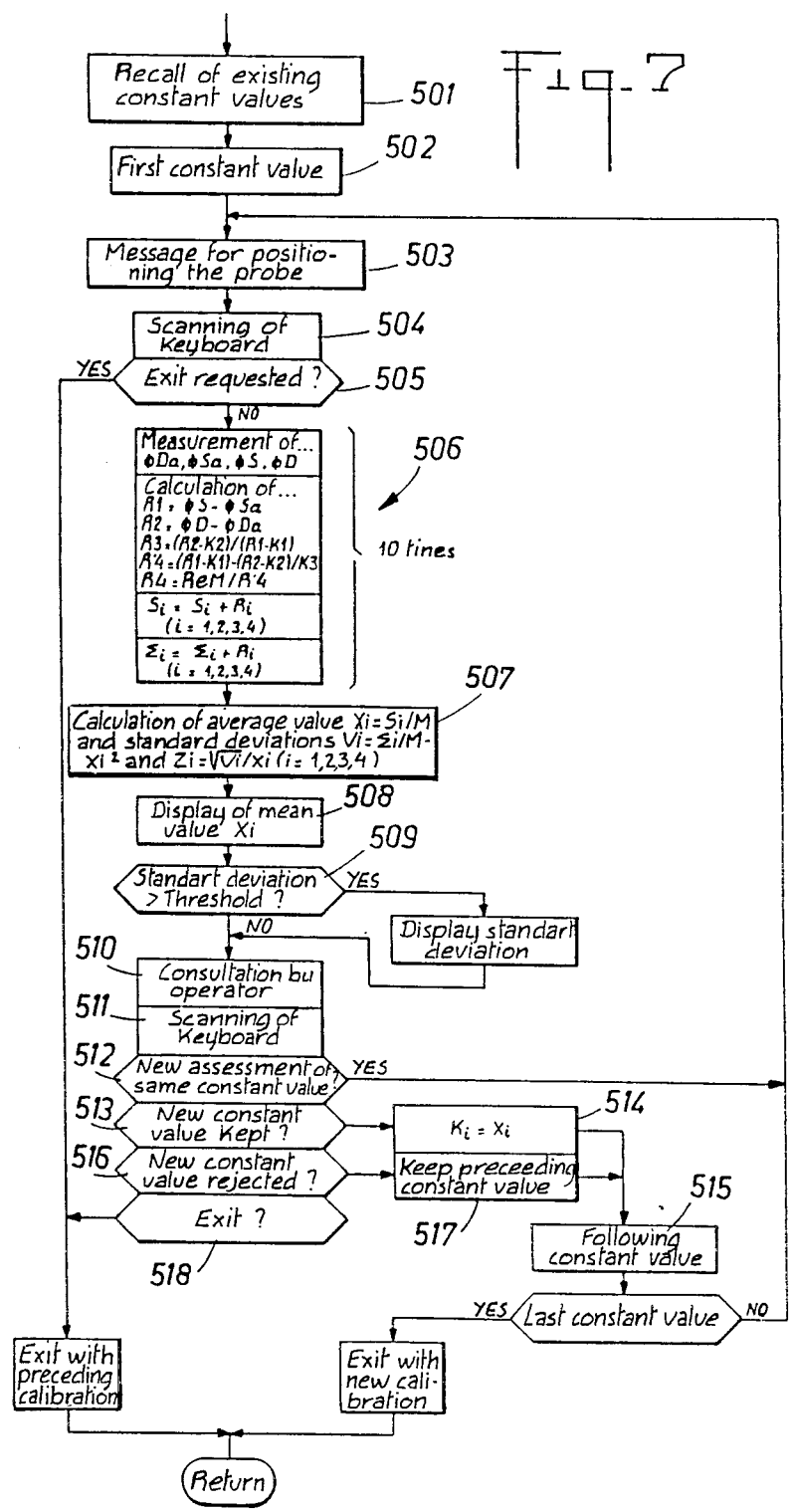

SKIN REFLECTANCE MEASURING APPARATUS

This application is a continuation, of application Ser. No. 849,446, filed 4/8,86 now abandoned.

The present invention relates to a skin reflectance measuring apparatus.

BACKGROUND OF THE INVENTION

The measurement of skin reflectance finds a particular application in pathology and in cosmetology. In particular, skin reflectance may be associated to other parameters such as the rate of secretion of sebum. The measurement of reflectance then becomes useful in the study of seborrhea. It may also present an advantage for studying other skin diseases such as lichen, SSM. . . . In cosmetology, the invention finds an application in measuring the effect of products known as "anti-reflectance" products for greasy skins, particularly for making efficiency-aimed tests. Another application of the present invention could be the grading of different types of skins.

Various methods and devices already exist for measuring surface reflectance, for example in the industry of paints and varnishes, in order to determine the characteristics of reflection of coated surfaces. It has also been proposed to use reflectance measurement to determine a surface finish.

All said known methods and processes which are used in industry are not applicable to the measurement of skin reflectance.

A first problem to be solved with this particular application is the problem of influence of color. Indeed, with the known devices which can only measure the specular reflection, the results obtained for different surfaces are only comparable if the surfaces are all of the same color.

To overcome the effect of color, it has been proposed to substitute to the specular reflection absolute measurement, a relative measurement between specular reflection and diffuse reflection. However, the known devices using such relative measurement remain inappropriate for measuring skin reflectance.

Indeed, the apparatuses used in industry, generally comprise optical systems with focusing lenses which require an accurate positioning of the measuring apparatus with respect to the surface of which the reflectance is being measured. It is then necessary for said surface to be flat and for the measuring area to be, in general, of relatively large dimensions.

Yet, in the case of the skin, the measuring area has to be relatively small in order to keep the characteristics of the skin uniform in that area and to make the measurement on as flat a surface as possible, without changing the characteristics to be measured by a flattening of the skin.

It is also important to have a measuring apparatus which is easy to handle and requires no higher accurate positioning with respect to the skin.

SUMMARY OF THE INVENTION

It is therefore the object of the present invention to propose a reflectance measurement apparatus which is specifically adapted for measuring the reflectance of the skin.

This object is reached with an apparatus which, according to the invention, comprises:

a probe comprising a casing of which one face, which will be in contact with the skin, is provided with an aperture, a flexible connection in fiber optics, comprising at least three optical conductors which, at a first end, are secured in the casing of the probe such as to face the aperture thereof, the first and second conductors having their first end portions directed respectively in a first and a second directions which are symmetrical to each other with respect to an axis extending normally through the aperture, while the third conductor has its first end portion directed in another direction than said second direction, a measuring device comprising: light emitting means optically coupled to a second end of said first conductor; light receiving means optically coupled to a second end of said second conductor to produce a first signal representing the specular reflection, and to a second end of said third conductor to produce a second signal representing part of the non-specular or diffuse reflection; and processing means connected to said light emitting and receiving means, and provided with correcting means to compensate for variations in the emitted light and for the influence of ambient light, said correcting means producing a relative reflectance signal from the measured values of specular reflection and diffuse reflection, and a display device receiving the reflectance signal to indicate the amplitude of said signal.

The structure of the measuring apparatus according to the invention, such as defined hereinabove, with a probe connected to a measuring device via a flexible connection in fiber optics, presents many advantages.

The use of fiber optics having their end secured inside the casing of the probe in a relatively fixed configuration, permits the miniaturization of the probe. It becomes, as a result, possible to carry out measurements on reduced surfaces and, in particular, on surfaces less than 1 cm2, for example surfaces between 10 and 50 mm2. This also makes the apparatus readily usable since the probe is of reduced dimensions and is connected to the rest of the apparatus by way of a flexible connection. Such readiness of use is further increased due to the fact that, contrary to the systems using optical means with beam focusing lenses and requiring an extremely accurate positioning of the apparatus on a flat surface, the apparatus according to the invention can tolerate a few degrees of deviation of relative position between the probe and the skin surface.

The correction of variations in the intensity of the emitted light and in the effect of the ambient light makes it possible to obtain a very accurate measurement without very strict operational conditions.

The means for correcting variations in light intensity can be in the form of a circuit for regulating a source of light of the emitting means, using servo-control means.

As a variant, means may be provided for measuring the intensity of the light produced by the emitting means in order to compensate for any variations occurring in that intensity, directly at the level of the signals produced by the reflected light receiving means.

The compensation for the effect of ambient light is advantageously achieved by conducting measurements according to the "synchronous detection" principle, namely by carrying out cycles of measurements during which the specular reflection and the diffuse reflection are measured when the light-emitting means is operative and when the light-emitting means is inoperative.

To control the course of said measurements and to process the results, the measuring device advantageously uses digital processing means such as a microcomputer.

It will be further noted that the display of the reflectance not only enables the operator to view immediately the value that he is seeking, but also helps in correctly positioning the probe.

The resulting reflectance is a relative value worked out from measurements of the specular reflection and of the diffuse reflection, for example the difference or the quotient between the measured values of specular and diffuse reflection. The difference is preferred to the quotient insofar as it introduces less scale distortion with respect to the judgement of the skin reflectance made by eye. A scale of reflectance may be defined from a measurement of a matt surface of reference (unit 1) and of a calibrated mirror (unit $10^n$, n being an integer above 0).

BRIEF DESCRIPTION OF THE DRAWINGS

The invention will be more readily understood on reading the following description with reference to the accompanying drawings, in which:

FIGS. 6 and 7 are flow charts of the operations carried out under the control of the digital processing means for, respectively measuring and calibrating.

DESCRIPTION OF THE PREFERRED EMBODIMENT

Figure 1:
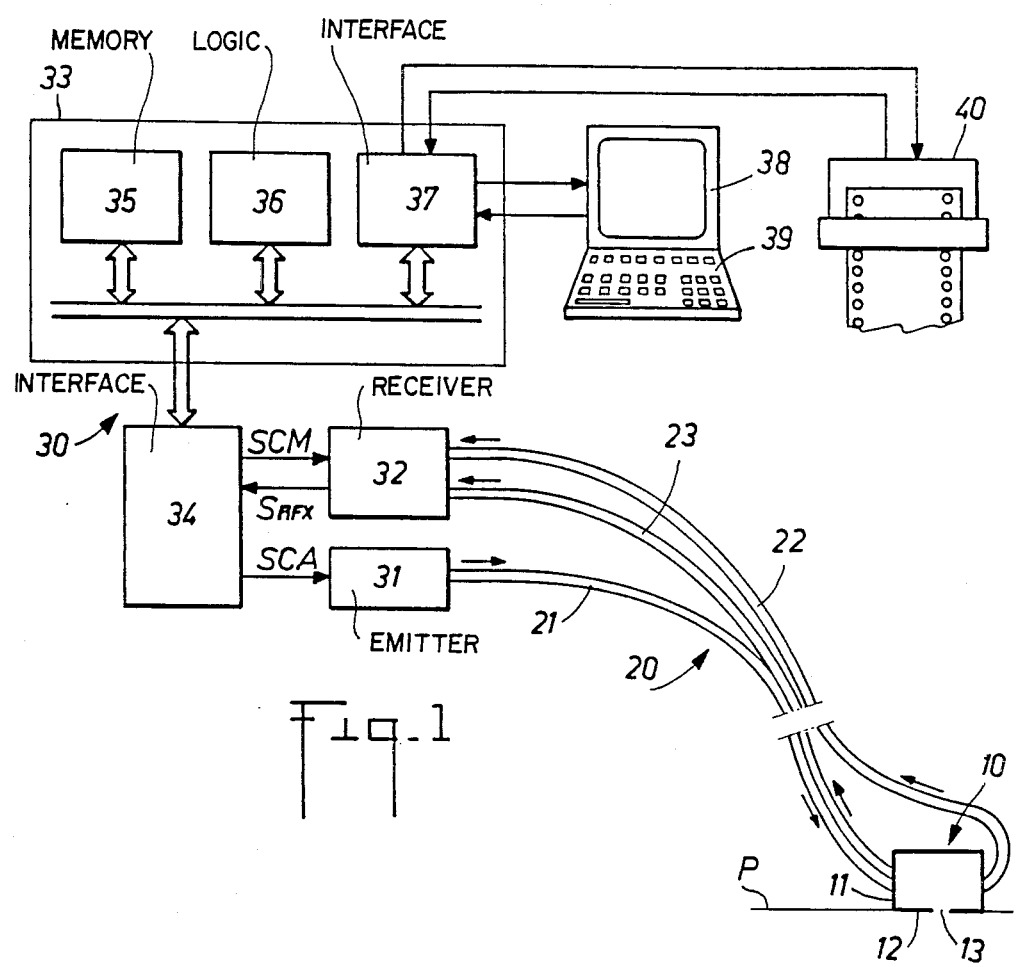
FIG. 1 is a general diagram of one embodiment of a reflectance measuring apparatus according to the invention.

The apparatus illustrated very diagrammatically in FIG. 1. comprises a probe 10, a measuring device 30 and a flexible connection 20 in fiber optics connecting the measuring device to the probe 10.

The probe 10 is designed to be placed in contact with the skin P in order to light up the part of the skin surface requiring to be examined.

The connection 20 comprises three optical channels 21, 22, channel 21 conveys to the probe the light produced from a light-emitting device 31 in order to illuminate the skin surface to be examined. Channel 22 transmits to a receiving device 32 the light reflected specularly (normally) by the examined part of surface whereas channel 23 transmits to the receiving device part of the light reflected in non-specular or diffuse manner. In the illustrated example, the diffuse reflection is measured in the direction opposite to the direction of incidence of the light on the surface to be examined. Channels 21 and 23 can therefore be re-grouped, at least at their end portions connected to the probe, into a bi-directional optical cable.

The emitting 31 and receiving 32 devices are connected to a control and processing device 33 via an interface circuit 34.

Said device 31 comprises means of regulating the intensity of the emitted light and is operated by control signals issued by the processing device 33.

The receiving device 32 comprises photo-electrical transducers working out electrical signals representing the normal reflection and the diffuse reflection. Said signals are transmitted to processing device 33 through the interface circuit 34, this transmission being achieved under the control of signals produced by the processing device.

In conventional manner, said processing device 33 comprises memory circuits 35, an arithmetical and logical unit 36 and interface circuits 37 permitting the connection with a display device 38, such as a cathod ray tube, with a keyboard 39 and with a printer 40. The processing device may be constituted by any of the existing micro-computers, therefore it will not be described any further herein.

Supply of the different circuits of the apparatus is ensured by supply circuits (not shown).

Figure 2:
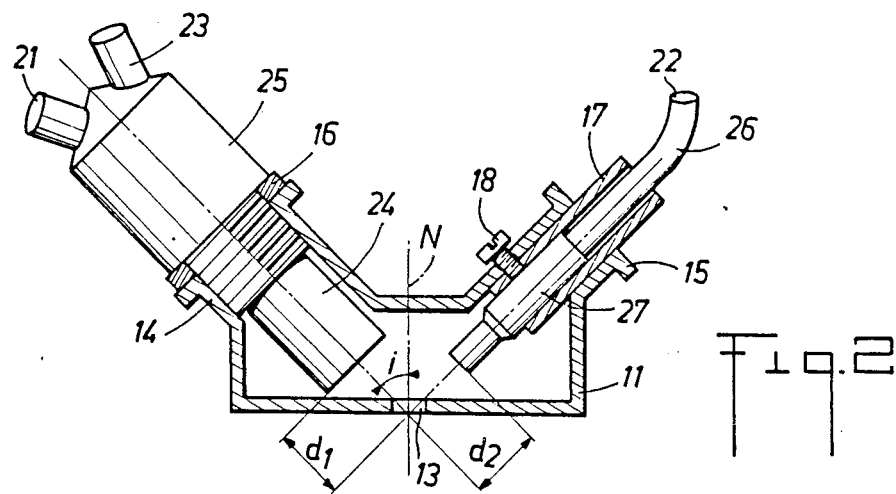
FIG. 2 is a more detailed cross-section of the probe of the apparatus shown in FIG. 1.

FIG. 2 is a diagrammatical cross-section showing the probe 10 in more details.

Said probe 10 comprises a casing 11 of which the front face 12 is provided in its center with an opening 13 such as of circular shape. The casing also presents two connecting parts 14, 15 in which are respectively secured the ends of channels 21 and 23 and the end of channel 22. Channels 21, 23 are re-grouped at their ends into a bidirectional optical cable 24 provided with an end socket 25 screwed into the connecting part 14, whereas optical cable 26 forming the channel 22 is provided with a ring 27 and is inserted in a tubular guide 17 housed in the connecting part 15.

The axis of optical cable 24, namely the axis of connecting part 14, traverses the center of aperture 13 and is inclined with respect to the perpendicular N to the front face 12 of an angle i, said angle i corresponding to the angle selected for the incidence under which the part of skin surface to be examined is illuminated. In the illustrated example, the angle of incidence i is equal to about 45°, but another value could also be selected. The axis of optical cable 26, namely the axis of connecting part 15 is symmetrical to the axis of cable 24 with respect to the perpendicular N traversing the center of aperture 13 since channel 22 is designed to pick up the normally reflected light.

Cables 24 and 26 are secured to the casing 11 in such a way that the ends of the fiber optics composing them are at predetermined distances d1 and d2 from the center of aperture 13. Adjustment of the position of the end of cable 24 is achieved by interposition of wedges 16 between the socket 25 and the connecting part 14 whereas the end of cable 26 is fixed in the required position in the guide 17 by a locking screw 18 traversing the connecting part 15 and resting against the ring 37. By way of example, distances d1 and d2 are about 20 mm.

The use of a flexible connection composed of fiber optics of which the ends are secured to the probe, presents several advantages. For example, the probe may be small, its overall dimensions being determined by the connecting means of the optical cables. Moreover, the probe has no optical elements such as lenses which require high positioning accuracy.

The measuring area, determined by the size of aperture 13 may then be small enough to allow significant measurements over a surface with as little rigidity and uniformity as the skin. For example, the surface of the measuring area may be between 10 and 50 mm2, such as about 25 mm2. The miniaturization of the probe and its flexible connection with the rest of the apparatus, also allow ready handling for taking measurements over different areas of the skin surface.

Figure 3:
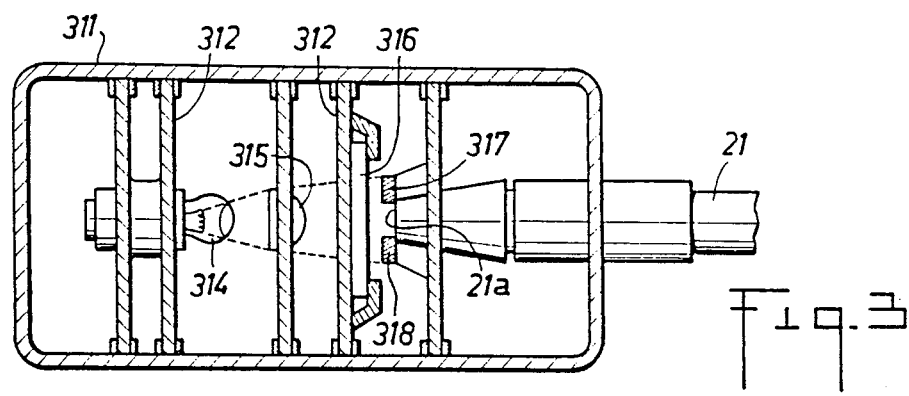
FIG. 3 illustrates in more detail the structure of the emitter of the light emitting means of the apparatus shown in FIG. 1.

FIG. 3 diagrammatically illustrates the structure of the emitter of the light emitting device 31.

Said emitter comprises a casing 311 to which is connected the starting end of optical channel 21. Said casing 311 is provided with walls 312 used as support for the different elements housed in the casing. The light source is a lamp 314 with tungsten filament. The beam produced by the lamp is focussed by means of a lens 315 in order to obtain an adequate light intensity at the input 21a to optical channel 21. An infrared filter 316 may be interposed between the lamp 314 and the input to optical channel 21 in order to carry out measurements within the field of the infrared-free visible light. Two photodiodes 317, 318 are placed on both sides of the input to optical channel 21 so as to supply signals representing the light intensity at that input. Photodiodes 317 and 318 are connected to a circuit 319 for regulating the light intensity produced by lamp 314.

Regulation circuit 319 (FIG. 4) comprises a source of voltage consisting of a transistor T1 of which the collector is at potential $+V$ of a supply source and the emitter is connected to a terminal at the reference potential (earth) via the lamp 314. Photodiodes 317, 318 are connected to an amplifier circuit AMP which delivers a voltage $V_{MES}$ representing the real intensity of the light beam applied to the input of channel 21. Voltage $V_{MES}$ is compared to a reference voltage $V_{REF}$, supplied by a voltage-adjustable generator SV; the comparison is carried out by means of a differential circuit CP which delivers a voltage $V_{COM}$ which is function of the difference between $V_{REF}$ and $V_{MES}$. The voltage $V_{COM}$ is applied to the base of T1 and determines the voltage in the lamp 314 so as to return towards zero the difference between voltages $V_{REF}$ and $V_{MES}$.

The circuit 319 receives a start control signal SCA applied via a resistor R1 to the base of a transistor T2. The emitter thereof is connected to earth whereas its collector is connected, on the one hand, to the voltage source $+V$ via a resistor R2 and, on the other hand, to the base of a transistor T3 via a resistor R3. Transistor T3 has its emitter-collector circuit connected between the base of T1 and the earth. When the start control signal is at a level between the triggering signal of transistor T2 (SCA=0, or low logic level), transistor 2 is in the OFF state, but transistor T3 is in the ON state, bringing the base of T1 to the earth potential; lamp 314 is switched off. When the ON control signal exceeds the triggering threshold of T2 (SCA=1, or high logic level), transistor T2 is turned to the ON state, this keeping T3 in the OFF state and lamp 314 is switched on, the intensity of the current through the lamp being determined by $V_{COM}$.

Figure 4:
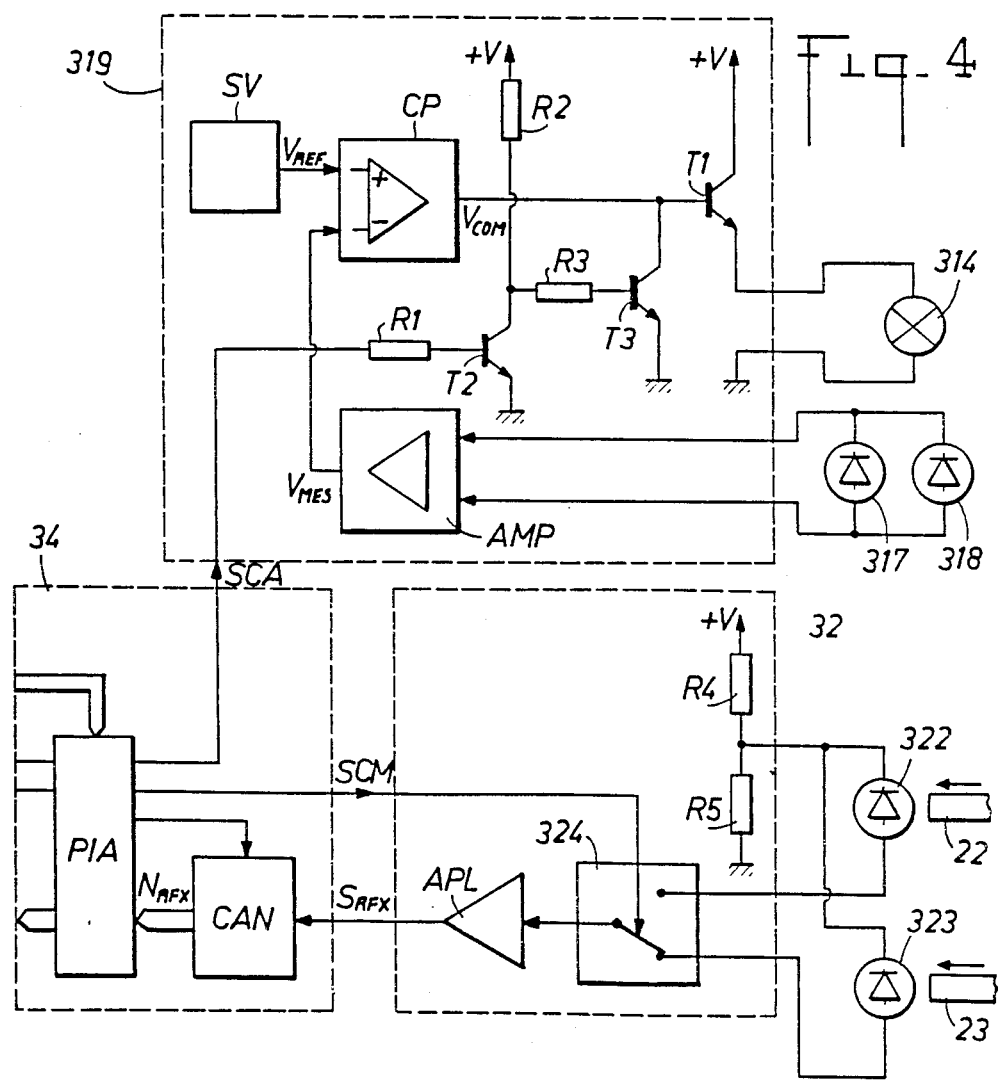
FIG. 4 is a diagram of the circuits of emitting and receiving means and of the interface circuit of the apparatus shown in FIG. 1.

FIG. 4 also shows the circuit of receiving device 32.

Two photodiodes 322, 323 receive light beams transmitted respectively by optical channels 22, 23. Diodes 322, 323 are silicon diodes connected in reverse. The cathodes of diodes 322, 323 are connected to the middle point of a voltage divider formed by two resistors R4, R5 connected in series between the earth and a terminal of potential V. Diodes 322, 323 thus produce a voltage substantially proportional to the intensity of the picked up light beams. The anodes of diodes 322, 323 are connected to two input contacts of an analog switch 324 of which the output contact is connected to the input of a logarithmic amplifier APL producing an analog signal $S_{RFX}$ representative of the specular reflection or of the diffuse reflection, depending on the position of switch 324. The use of a logarithmic amplifier procures greater dynamics. Moreover, the human eye constituting a logarithmic type receiver, the measuring apparatus makes it possible to come closer to the visual judgement which it is required to quantify.

The receiving device receives a switch control signal SCM controlling the position of the switch. For example, when signal SCM has a high logic level (SCM=1), switch 324 connects photodiode 232 with amplifier APL to measure the specular reflection, whereas when signal SCM has a low logical level (SCM=0) switch 234 connects photodiode 233 to amplifier APL to measure the diffuse reflection.

Interface circuit 34 comprises an analog-to-digital converter CAN which receives the signal $S_{RFX}$ to convert it in the form of a digit word $N_{RFX}$ of n bits. A connection circuit PIA ("parallel interface adapter") is interposed between the converter CAN and the microcomputer 33. Said circuit PIA also transmits signals SCA and SCM as well as the control signals of converter CAN. Circuit PIA is controlled in known manner by control signals produced by the micro-computer.

The emitting and receiving devices are controlled to produce a reflectance measurement from the specular and diffuse reflection values; in the illustrated case, the worked out value represents the difference between the specular reflection intensity and the diffuse reflection intensity. Moreover, in order to take into account the influence of ambient light, the reflection is measured according to a principle of "synchronous detection" namely by alternately controlling the switching on and off of the light source.

The light flux $\Phi S$ carried by channel 22 (specular reflection is composed of flux $\Phi Sp$ effectively reflected by the skin, of flux $\Phi Sa$ coming from the outside (ambient light) and from leaks from the detectors, and of flux $\Phi Ss$ sent back by the casing of the probe. Likewise, the light flux $\Phi D$ carried by channel 23 (diffuse reflection) comprises components $\Phi Dp$, $\Phi Da$ and $\Phi Ds$.

During a measuring cycle, the flux $\Phi Da$, $\Phi Sa$ are successively measured by actuating switch 324, the lamp being switched off, then after switching the lamp on, the flux $\Phi S$ and $\Phi D$ are measured successively by actuating the switch 324.

The desired reflectance Re is equal to:

$$Re = \Phi Sp - \Phi DP = (\Phi S - \Phi Sa - \Phi Ss) - (\Phi D - \Phi Da - \Phi Ds)/K,$$

K being a corrective factor taking into account the geometry of the probe and of the optical channels 22, 23 since the reflectance is assessed by differences between intensities of the specular and diffuse reflections, and not by differences between flux.

The quantities $\Phi Ss$, $\Phi Ds$ and K are determined by calibration. By placing the probe before a light trap (instead of the skin) $\Phi Sa + \Phi Ss$ and $\Phi Da + \Phi Ds$ are measured, when the lamp is switched on, and $\Phi Sa$ and $\Phi Da$ are measured when the lamp is switched off, wherefrom $\Phi Ss$ and $\Phi Ds$ are deduced. The value of K is thereafter determined by placing the probe before a matt surface used as a reference of nil reflectance (Re=0) by measuring $\phi D$, $\Phi S$, $\Phi Da$ and $\Phi Ss$, and by calculating:

$$K = (\Phi D - \Phi Da - \Phi Ds)/(\Phi S - \Phi Sa - \Phi Ss).$$

A scale coefficient SC is also determined by placing the probe before a reflecting surface of reference such as a calibrated mirror at 80% reflection, the reflectance being then arbitrarily fixed to a predetermined value ReM (for Example 1000). After measuring $\phi D$, $\Phi S$, and $\Phi Ss$, the coefficient SC is determined by dividing ReM by the quantity:

$$(\Phi S - \Phi Sa - \Phi Ss) - (\Phi D - \Phi Da - \Phi Ds)/K.$$

The values of $\Phi Ss$, $\Phi Ds$, K and SC, determined by calibration, are stored in the memory circuits 34 of the micro-computer.

Figure 5:
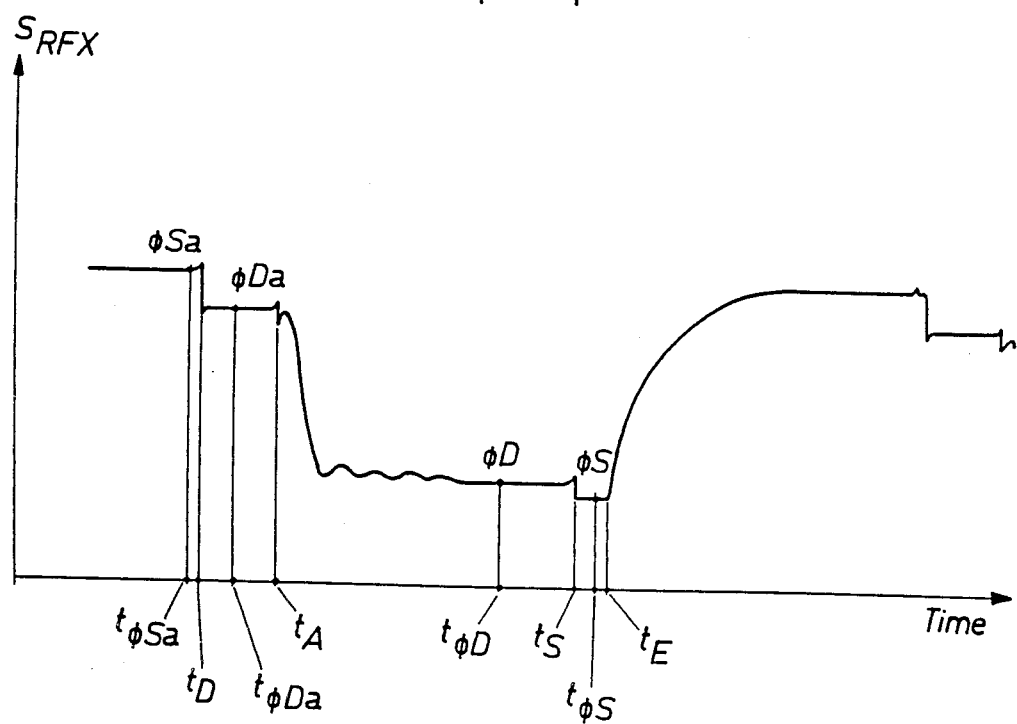
FIG. 5 illustrates the variation in time of the output voltage of the receiving means during a measuring cycle.

FIG. 5 shows the variation in time of voltage $S_{RFX}$ in output of logarithmic amplifier APL. The times $t_{\Phi Sa}$, $t_{\Phi Da}$, $t_{\Phi D}$, $t_{\Phi S}$ correspond to the times of measurement of quantities $\Phi Sa$, $\Phi Da$, $\Phi D$ and $\Phi S$. The times $t_A$ and $t_E$ correspond to the switching on and switching off of the lamp, whereas times $t_S$ and $t_D$ correspond to the times of actuation of switch 234, respectively, towards photodiode 232 (specular reflection) and towards photodiode 233 (diffuse reflection).

The successive measuring cycles are performed under the control of the micro-computer. The duration of one cycle may be less than 1 sec., for example around 0.7 sec., said duration being for example function of the times necessary for the stabilization of the lamp when this is switched on and off. The values of reflectance Re calculated during successive measurement cycles are displayed as successive positions of a cursor on the screen of tube 38. The operator can thus correct any incorrect positioning of the probe by observing the position variations in y-axis of the cursor when moving the probe slightly. Instantaneous display of the reflectance calculated value thus contributes to positioning the probe. The reflectance value finally retained may be a mean value worked out from the results of a predetermined number of measurement cycles. Said final value may be edited on the printer 40 and is displayed on the screen. The resulting reflectance value is recorded in a computer file which may contain other information concerning the patient whose skin is being examined, the date of examination and any special conditions of examination. The recorded information may be edited on paper via the printer, at the operator's request.

The main programme including the operations of initialization of the system and the subroutines of recording on file and file readout are not specific phases of the proposed application; therefore they are not explained hereinafter in details.

The measuring and calibrating operations use programmes such as per flow-charts illustrated in FIGS. 6 and 7.

The measuring operation consists in the following phases:

initialization of the graph, and tracing of the outline of the screen with a view to displaying the measurement results as a curve representing the variation of the reflectance (phase 400);

positioning of the cursor in abscissa L=1 on the screen (phase 401);

scanning of the keyboard (phase 402);

if the operator, by actuating the keyboard, requests the exit of the subroutine (test 403), return to the main programme;

if the operator, by actuating the keyboard, requests an integration on the reflectance values obtained during the successive cycles of measurement (test 404), a subroutine (420) is called during which a test is carried out on the positioning of an averaging indicator ($E = -1!$), so as, in the affirmative, to arrive at end of averaging, to return indicator E to zero, and to return to the programme, and, in the negative, to bring sum S and parameter N to zero, to position E to $-1$ and to return to the programme;

measurement of the flux $\Phi Da$, the signals SCA and SCM being in zero position, and readout of the corresponding digital value (phase 405);

switching from channel 23 to channel 22 by placing SCM in position 1, measurement of flux $\Phi Sa$ and readout of the corresponding digital value (phase 406);

switching on of the lamp by bringing SCA to position 1, measurement of the flux $\Phi S$ and readout of the corresponding digital value (phase 407);

switching from channel 22 to channel 23 by bringing SCM to position 0; measurement of $\Phi D$ and readout of the corresponding digital value (phase 408);

calculation of Re from the readout values of $\Phi Da$, $\Phi Sa$, $\Phi S$ and $\Phi D$, and of the pre-recorded values of $\Phi Ss$, $\Phi Ds$, K and FE (phase 409)

if an integration is called (test 410) calling of a summation subroutine 430 including updating of sum S ($S = S + Re$), incrementing of N ($N = N + 1$), calculation of an "instant mean value" of reflectance $M_i(Re) = S/N$, control of the display on the screen of the digital value of $M_i$ (Re) and return to the programme;

editing of the digital values of Re or, optionally, of $M_i(Re)$ (phase 411);

graphic display of the digital value of Re by control of the ordinate of the cursor on the screen (phase 412);

incrementing of the abscissa of the cursor on the screen: $L = L + 1$ (phase 413);

if the value of L is equal to the maximum abscissa possible $L_{MAX}$ (test 414), clearing of the screen (phase 415) and return to initialization of the graph, if not, return to phase 402;

The calibration operation consists in the following phases:

recall of existing constant values (phase 5 1)

passage to first constant value (phase 502);

display on the screen of a message (phase 503) for placing the probe before the surface corresponding to the constant value to be determined (light trap, matt surface of reference, reference mirror);

scanning of the keyboard (phase 504);

if the operator, by actuating the keyboard, requests the exit of the subroutine (test 505), return to the main programme without changing the calibration;

for every constant to be determined K1 to K4 (K1=$\Phi Ss$, K2=$\Phi Ds$, K3=K and K4=SC), performance of M successive cycles of measurement, for example 10 cycles, (phase 506) each one including:

measurements of flux $\Phi Da$, $\Phi Sa$, $\Phi S$ and $\Phi D$ (phases 405 to 408 of the aforesaid measuring programme);

the calculation of quantities $R1 = \Phi S - \Phi Sa$, $$R2 = \Phi D - \angle Da, \ R3 = (R2 - K2)/(R1 - K1),$$
$$R'4 = (R1 - K1) - (R2 - K2)/K3$$

and $$R4 = ReM/R'4;$$

updating of sum Si by:

$$Se = Si + Ri \ (i = 1, 2, 3 \text{ or } 4);$$

and updating of sum $\Sigma I$ by $$\Sigma i = \Sigma i + R^2 \ (i = 1, 2, 3 \text{ or } 4);$$

calculations of mean value and standard deviation for every constant (phase 507), namely mean value $Xi = Si/M$, standard deviation $Vi = \Sigma i/m - Xi^2$ and reduced standard deviation $$Zi = \rightleftarrows Vi/Xi \ (i = 1, 2, 3 \text{ or } 4);$$

display of calculated mean value X (phase 508);

if the reduced standard deviation is greater than a predetermined threshold (test 509), it is displayed on the screen, if not, then direct passage to the next phase;

consultation by the operator (phase 510)

scanning of the keyboard (phase 511)

if the operator, by actuating the keyboard, requests a new assessment of the same constant (test 512), return to phase 503;

if the operator, by actuating the keyboard, requests that the new constant be kept (test 513), then $Ki = Xi$ (phase 514) and passage to the next constant (phase 515);

if the operator, by actuating the keyboard, refuses the value Xi (test 516), then the actual value of the constant is kept (phase 517) with passage to the next constant (phase 515);

if the operator, by actuating the keyboard, requests the exit (test 518), then return to the main programme without modifying the calibration;

when passing to the next constant (phase 515) and if the four constants have not yet been calculated (test 519), return to phase 503;

if all the constants have been calculated, exit with modification of the calibration and return to the main programme.

Tests have been conducted with a mesuring apparatus suc as described hereinabove by using a scale of reflectance Re ranging from 0 for the matt surface of reference to 1000 for the reflecting surface of reference (mirror with 80% reflection).

The measurements taken on 34 people have given reflectance values within a range of 8 to 12.5 for the fore-arm and from 6 to 13.9 for the forehead.

In the case of people (7 cases) whose skin appears to be greasy to the eye, the mean reflectance value measure on the forehead has been 11.7, to be compared with the general means value of 9.56 obtained from measurements taken in 32 random cases. Moreover, measurements taken on five subjects have shown a deviation of 5.4 between the mean reflectance values obtained before and after application of "Vaselin" on the fore-arm.

These results show the effective correlation between the visual aspect of reflectance and the measurements taken, thereby justifying the use of the measuring apparatus according to the invention as an "objective"means of quantifying the reflectance of the skin.

What is claimed is:

1. A skin reflectance measuring apparatus, comprising:

(a) a probe comprising a casing enclosing a chamber and having a front wall portion with a surface for contacting said skin, said wall being provided with an aperture which defines a measuring area for measuring the reflectance of a limited portion of said skin, said measuring area having a surface area between 10 and 50 mm$^2$;

(b) flexible fiber optics connection means comprising at least three optical conductors, each conductor having a first end secured in said casing and protruding into said chamber in the direction said aperture and at a fixed distance thereof, without any optical device being interposed between the first end of each conductor and said aperture, a first and a second of said conductors having their first end portions directed respectively in a first and second direction which are symmetrical to each other with respect to an axis extending normally through said aperture, and a third of said conductors having its first end portion extending in another direction than the second direction;

(c) a measuring device comprising light emitting means coupled to a second end of said first conductor to illuminate said measuring area through said aperture, said light emitting means having a control input for receiving a control signal to turn the light emitting means into operative or non-operative state; light receiving means optically coupled to a second end of the second conductor to produce a first signal representative of specular reflection from the skin through said aperture, and to a second end of the third conductor to produce a second signal representtive of non-specular or diffuse reflection from the skin through said aperture; and circuit means connected to said light emitting means and light receiving means to produce relative reflectance information from the measured values of specular reflection and diffuse reflection represented respectively by said first and second signals, said circuit means comprising:

first compensating means to compensate for variations in the intensity of emitted light, processing means having signal input means to receive said first and second signals and an output connected to said control input of the light emitting means, said processing means controlling automatic carrying out of successive measurement cycles each one including two measurements of the value of specular reflection, respectively when the light emitting means is operative and when the light emitting means is not operative, and two measurements of the value of diffuse reflection, respectively, when the light emitting means is operative and when the light emitting means is not operative, and said processing means having calculation means to compensate the values of specular and diffuse reflections when the light emitting means is operative for the influence of ambient light represented by the values of specular and diffuse reflections measured when the light emitting means is not operative, and memory means to store values of specular and diffuse stray reflections measured by placing said face of the probe casing into contact with a light absorbing surface, said processing means having calculation means to further compensate the values of specular and diffuse reflections measured when the light emitting means is operative, for the influence of stray light reflected by the probe and represented by said stored values of specular and diffuse stray reflections, and means for calculating reflectance information based upon measured values of specular and diffuse reflection after compensating said values for the influence of ambient light and stray light; and (d) display means connected to the measuring device to receive said reflectance information and to provide a visual representation thereof.

2. An apparatus as claimed in claim 1, wherein the first end portions of the first and third conductors extend in the same direction and are secured to the casing of said probe by means of the same connector.

3. An apparatus as claimed in claim 1, wherein:

said light emitting means comprises a light source and voltage supply means for supply said light source with an adjustably controlled voltage, and said first compensating means comprises a photoelectric detector arranged to receive light emitted by said light source and to produce a signal representative of said emitted light; and a regulation circuit having an input connected to said photoelectric detector to receive the signal produced thereby, and an output connected to said voltage supply means to control the voltage supplied to said light source in order to keep the intensity of light emitted by said light source at a substantially constant value.

4. An apparatus as claimed in claim 1, wherein said circuit means comprises processing means to produce said relative reflectance information by the difference between the compensated measured values of specular reflection and of diffuse reflection.

5. An apparatus as claimed in claim 1, wherein:

said light receiving means comprises first and second photoelectric converter means respectively coupled to the second ends of said second and third optical conductors; and said circuit means comprises analog-to-digital converter means having a digital signal output connected to said processing means and an analog signal inout, and controllable switching means inserted between said analog signal input and said photoelectric converter means, said processing means generating a signal to control said switching means to connect said analog signal input of the analog-to-digital converter means either with the first photoelectric converter means to measure the value of specular reflection, or with the second photoelectric converter means to measure the value of diffuse reflection.

6. An apparatus as claimed in claim 1, wherein:

said light receiving means comprises photoelectric converter means coupled to the second ends of said second and third optical conductors to produce signals representative of said specular and diffuse reflections; and said circuit means comprises logarithmic amplifier means for receiving and amplifying said signals produced by the photoelectric converter means.

* * * * *